United States Patent

Hart

[11] Patent Number: 5,916,232
[45] Date of Patent: Jun. 29, 1999

[54] ASYMMETRICAL OBTURATOR

[75] Inventor: Charles C. Hart, Huntington Beach, Calif.

[73] Assignee: Applied Medical Resources Corporation, Laguna Hills, Calif.

[21] Appl. No.: 08/949,123

[22] Filed: Oct. 10, 1997

[51] Int. Cl.[6] ................................................. A61B 17/00
[52] U.S. Cl. ......................................................... 606/185
[58] Field of Search ..................... 606/185, 184, 606/171–183, 167, 164, 174; 604/164, 264

[56] References Cited

U.S. PATENT DOCUMENTS

| 5,275,583 | 1/1994 | Crainich .................................. | 604/264 |
|---|---|---|---|
| 5,314,417 | 5/1994 | Stephens et al. ....................... | 604/264 |
| 5,318,580 | 6/1994 | Gresl, Jr. ................................ | 606/185 |
| 5,364,372 | 11/1994 | Danks et al. ............................ | 604/264 |
| 5,417,705 | 5/1995 | Haber et al. ............................ | 606/185 |
| 5,431,635 | 7/1995 | Yoon ...................................... | 606/185 |
| 5,441,041 | 8/1995 | Sauer et al. ............................. | 600/106 |
| 5,441,513 | 8/1995 | Roth ....................................... | 606/185 |
| 5,445,142 | 8/1995 | Hassler, Jr. ............................. | 600/105 |
| 5,467,762 | 11/1995 | Sauer et al. ............................. | 600/114 |
| 5,554,137 | 9/1996 | Young et al. ............................ | 604/264 |
| 5,554,167 | 9/1996 | Young et al. ............................ | 606/184 |
| 5,569,160 | 10/1996 | Sauer et al. ............................. | 600/114 |
| 5,569,288 | 10/1996 | Yoon ...................................... | 606/185 |
| 5,569,291 | 10/1996 | Privitera et al. ........................ | 606/185 |
| 5,569,292 | 10/1996 | Scwemberger et al. ................ | 606/185 |
| 5,591,186 | 1/1997 | Wurster et al. ......................... | 606/170 |
| 5,599,347 | 2/1997 | Hart et al. ................................ | 606/42 |
| 5,607,440 | 3/1997 | Danks et al. ............................ | 606/185 |
| 5,609,604 | 3/1997 | Schwemberger et al. ............. | 606/185 |
| 5,690,663 | 11/1997 | Stephens ................................ | 606/185 |

FOREIGN PATENT DOCUMENTS

0 701 799 A1  3/1996  European Pat. Off. .

*Primary Examiner*—Michael Buiz
*Assistant Examiner*—Vikki Trinh
*Attorney, Agent, or Firm*—Richard L. Myers

[57] ABSTRACT

An asymmetrical obturator adapted to be coupled with a trocar and to provide the trocar with characteristics for penetrating tissue forming a body wall. The obturator includes an elongate shaft which extends along a longitudinal axis between a proximal end and a distal end. The distal end of the shaft includes a first and a second longitudinal shaft portions, the first of which is distally configured with a sharp edge. The second shaft portion generally opposes the first shaft portion and is configured with a blunt distal tip. The first shaft portion and the second shaft portion are longitudinally slidable relative to each other between a cutting position and a safety position. In the cutting position, the second shaft portion is moved proximally relative to the first shaft portion to expose the sharp edge of the first shaft portion. In the safety position, the second shaft portion is moved distally relative to the first shaft portion to cover the sharp edge of the first shaft portion. A biasing element maintains the obturator in the safe position and an actuating mechanism allows the obturator to be temporarily moved into the cutting position.

11 Claims, 5 Drawing Sheets

ASYMMETRICAL OBTURATOR

FIELD OF THE INVENTION

This invention relates generally to trocar assemblies and more particularly, to obturators which form part of the trocar assembly and facilitate penetration of a body wall by the trocar assembly.

BACKGROUND OF THE INVENTION

A trocar assembly generally includes two major components, a trocar body and an obturator. The trocar body typically includes a cannula having a cylindrical configuration and a valve housing. When operatively disposed, the cannula of the trocar body extends across a body wall, such as the abdominal wall, to provide access into a body cavity, such as the abdominal cavity. The obturator typically includes an elongate body having a sharpened distal tip. Placement of the trocar body in the operative position is facilitated by the obturator and its sharp distal tip which actually punctures and penetrates the tissue forming the body wall.

The elongate body of the obturator is typically mounted in the trocar body with the sharp distal tip extending beyond the distal end of the trocar. As the trocar is pushed or otherwise moved through the body wall, the sharp distal tip functions to cut the tissue and provide and opening for the trocar. Once the trocar is operatively positioned, the obturator can be removed from the trocar body leaving the cannula to provide working-channel access into the body cavity.

It is certainly one of the primary purposes of the obturator to provide a sharp distal tip to facilitate the cutting of body wall tissue as the assembly penetrates the body wall. However, of equal importance, is the need to insure that the cutting stops once the body wall has been penetrated. It has been found that a relatively large force is required to cause the sharpened tip of an obturator to penetrate the body wall. However, once the sharpened tip penetrates the body wall, resistance to penetration is removed and the sharpened tip of the obturator is suddenly free to reach into the body cavity and cause additional cutting. Failure to stop this cutting action can result in considerable damage to interior organs and other tissues within the cavity.

In an effort to avert these dangers to the patient, trocars have been developed with a variety of safety features and devices. One common safety device includes a spring-loaded tubular safety shield which surrounds the shaft and the sharpened tip of the obturator. The distal end of the tubular shield presses against the skin as the sharpened tip of the obturator penetrates the body wall. When the obturator has formed an opening in the body wall of sufficient size that the tubular safety shield can pass therethrough, resistance to the movement of the tubular safety shield is removed. This allows the safety shield to spring forward and cover the sharpened tip. Once the sharpened tip is covered, the internal tissues and organs are protected from inadvertent cutting. An example of a trocar including such a safety shield is described and claimed in U.S. Pat. No. 4,535,773.

Unfortunately, trocars having these spring-loaded tubular safety shields require larger incisions. Particularly, the incision formed by the obturator generally must extend to the outer diameter of the tubular shield before the resistance of the tissue pressure is decreased to allow the shield to spring forward. These tubular shields also possess a relatively large mass which has required considerable time to move the shield into the forward or safety position. Tubular shields have also left a relatively large distal opening which has provided some access to the sharped tip of the obturator.

The sharpened tip of the obturator typically includes a blade having a symmetrical triangular form. These blades tend to form an opening which results in a wound consisting of three cuts each radiating from a central puncture or penetration point. While it is generally agreed that this blade configuration provides minimal entry force, it has been of recurring concern that the resulting wound can result in herniation, as well as other complications associated with wound closure and healing.

Obturators having single blade configurations have also been developed. These single blade obturators penetrate the body wall through a single incision which reduces the concerns about wound herniation, closure and healing. An example of an obturator having a single-blade configuration, is disclosed and claimed by Schwemberger et al. in U.S. Pat. No. 5,609,604. The obturator of this patent has a conical distal tip that is axially slotted to receive a planar blade which is movable between a distal exposed position and a proximal retracted position. However, the relatively heavy blade and supporting mechanism add significantly to the actuation time required for retraction. This actuation time leaves the blade exposed, potentially allowing undesired and unnecessary cutting to continue. This configuration also fails to provide an incision which accommodates the full diameter of the obturator. As a result, insertion forces required to penetrate the body wall tend to be relatively high.

SUMMARY OF THE INVENTION

These problems with the obturators and trocar assemblies of the past are overcome with the present invention, which in most embodiments includes an asymmetrical obturator having a single blade with a sharpened edge that extends across the full diameter of the obturator shaft. The resulting cut in the body wall eliminates the weak central flaps of a tri-cusped wound, and provides an easily suterable incision. Surprisingly, the force of entry of the obturator closely approximates that associated with the three-blade systems of the prior art.

The obturator of the present invention also satisfies the need for an obturator having a safety device which quickly and positively covers the sharpened edge of the blade, by providing an obturator shaft with two generally opposing longitudinal shaft portions. The single blade is affixed to a distal end of one of the shaft portions and the distal end of the opposing shaft portion is configured with a relatively blunt end. The shaft portions are configured to slide relative to each other along a longitudinal axis of the shaft such that the sharpened edge is exposed in one position and safely covered by the blunt end in a second position.

The present invention is generally directed to an obturator adapted to be coupled with a trocar and to provide the trocar with characteristics for penetrating tissue forming a body wall. The obturator includes an elongate shaft having at least two shaft portions which extend along a longitudinal axis between a proximal shaft end and a distal shaft end. A first shaft portion is fitted with a blade on its distal end. The blade has a planar surface with a sharpened distal edge and extends generally across the diameter of the shaft. A second shaft portion generally opposes the first shaft portion and is fitted with a blunt distal tip. The blunt distal tip extends generally across the diameter of the shaft and has a planar surface for slidable contact with the planar surface of the blade.

The first and second shaft portions are longitudinally movable relative to each other between a cutting position, wherein the distal end of the shaft is generally defined by the configuration of the sharpened distal edge of the first shaft portion, and a safe position, wherein the distal end of the shaft is generally defined by the blunt tip of the second shaft portion. More specifically, the blunt distal end may be moved proximally relative to the sharpened edge of the blade to expose the sharpened edge. Similarly, the blunt distal tip may be moved distally relative to the sharpened edge to cover the sharpened edge and to define the shaft with a blunt distal tip. The planar surface of the distal blunt tip is slid longitudinally relative to the planar surface of the blade between these relative position.

Each of the first and second shaft portions has an outer surface and an inner surface. The outer surfaces of the shaft portions define the outer surfaces of the obturator shaft, while the inner surfaces are slidable relative to each other to provide the distal end of the obturator with its alternative sharpened edge and blunt tip configurations.

In another aspect of the present invention, the obturator includes an elongate shaft having a longitudinal axis extending between a proximal end and a distal end. The distal end of the shaft includes a shaft tip having a first tip portion and a generally opposing second tip portion. The first tip portion extends along the longitudinal axis and includes one of a sharp distal tip end and a blunt distal tip end. The second tip portion also extends along the longitudinal axis and includes the other of the sharp distal tip end and the blunt distal tip end. The first and second tip portions are movable relative to each other along the longitudinal axis of the shaft.

An actuating mechanism is connected to the proximal end of the shaft and coupled to the second tip portion through the shaft. The actuating mechanism moves the first tip portion relative to the second tip portion. More specifically, the actuating mechanism moves the second tip portion longitudinally relative to the first tip portion between a first position, wherein the configuration of the shaft tip is primarily defined by the first tip portion, and a second position, wherein the configuration of the shaft tip is primarily defined by the second tip portion.

In yet another aspect of the present invention, the obturator has an elongate shaft including a first longitudinal shaft portion. This first shaft portion has a radial cross-section configured in the general shape of a section of a circle and is longitudinally movable relative to the remaining portion of the shaft. The first shaft portion is movable between a first or cutting position and a second or safety position. When in the cutting position, the first shaft portion is disposed proximally relative to the remaining portion of the shaft to expose a blade on the distal end of the shaft. The blade includes a sharp distal edge configured for cutting tissue and penetrating the body wall. When in the safety position, the first shaft portion is disposed distally relative to the remaining shaft portion to cover the sharp distal edge and inhibit the cutting of tissue by the distal end of the shaft.

A method for operating an obturator is also disclosed in a further aspect of the present invention. The method includes the step of providing an obturator having a shaft with an outer surface that extends between a proximal end and a distal end along a longitudinal axis. The shaft includes a first shaft portion which defines part of the outer surface and has an inner surface and a sharp distal tip. The shaft also includes a second shaft portion which also defines part of the outer surface and has an inner surface. However, the second shaft portion includes a blunt distal tip. The method includes the step of moving the inner surface of the first shaft portion in proximity to the inner surface of the second shaft portion between a first position wherein the distal tip of the shaft is characterized by the sharp distal tip of the first shaft portion, and a second position wherein the distal tip of the shaft is characterized by the blunt distal tip of the second shaft portion.

Typically, the obturator is inserted through the body of a trocar. This step may include passing the shaft of the obturator through the cannula until the distal end of the shaft is exposed beyond the distal end of the cannula. The obturator is then moved into the first or cutting position just prior to penetration of the tissue forming the body wall. This step generally includes moving an actuator or actuating mechanism coupled to the obturator shaft to an armed or cutting position. In this position, the second shaft portion is held proximally relative to the first shaft portion such that the sharp distal tip is exposed. Once the actuating mechanism senses pressure or resistance on the first shaft portion, the second shaft portion is forced forwardly along the longitudinal axis. This moves the blunt distal end over the sharp distal end and prevents further cutting of tissue.

This invention, together with the additional features and advantages thereof, which is only summarized in the foregoing passages, will become more apparent to those of skill in the art upon reading the description of the preferred embodiments, with reference to the following drawings.

DESCRIPTION OF THE PREFERRED EMBODIMENTS

Figure 1:
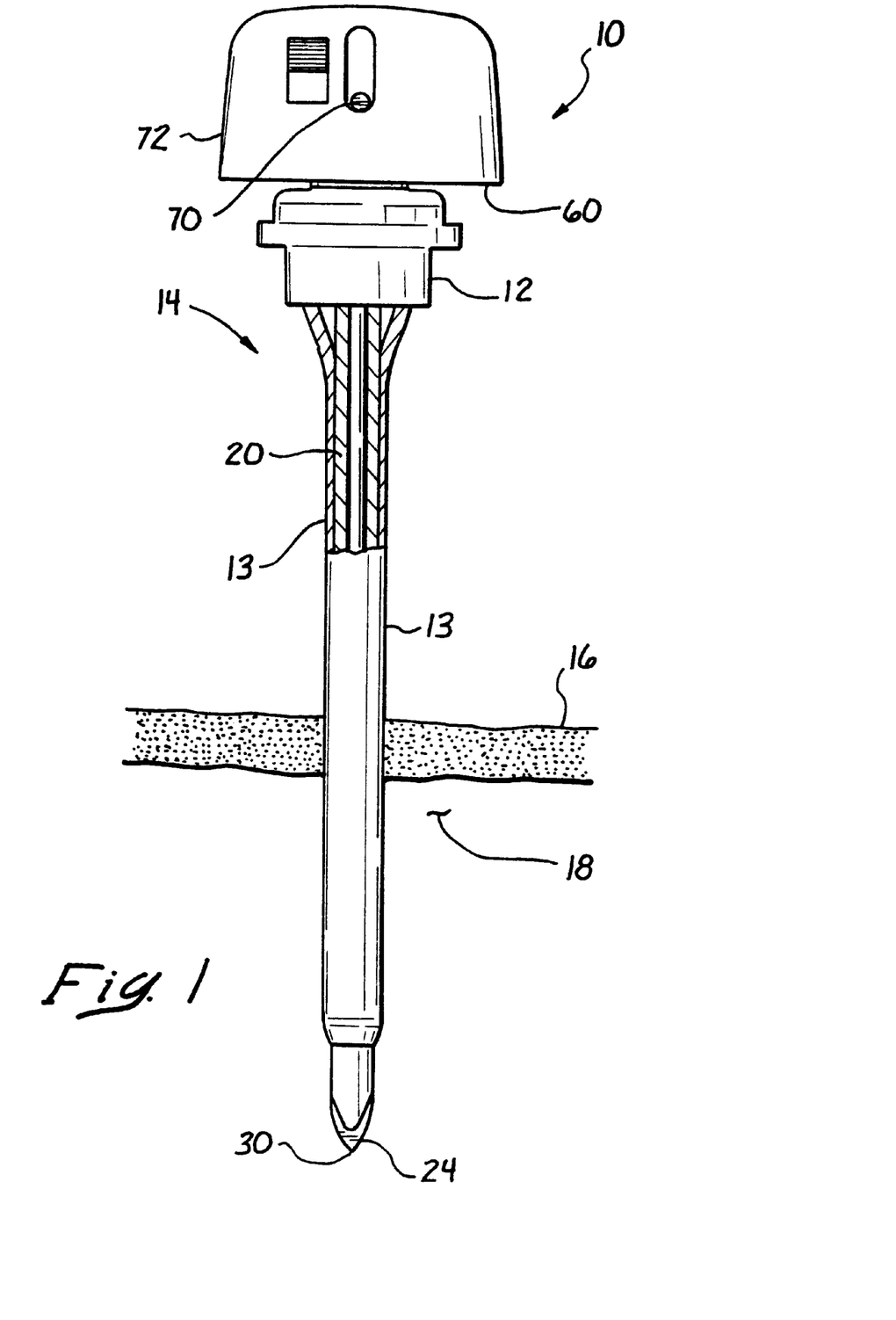
FIG. 1 is a perspective view of an embodiment of the obturator of the present invention shown inserted into a cannula to form a trocar assembly.

Referring now to the drawings, wherein like reference numerals designate identical or corresponding parts throughout the several views and embodiments, an obturator according to the principles of the present invention is illustrated in FIG. 1 and designated by the reference numeral 10. As shown, the obturator 10 is adapted for use with a trocar body 12, including a cannula 13, in order to form a penetrating trocar assembly 14. The obturator 10 is first inserted through the trocar body 12, including the cannula 13, prior to being inserted through tissue forming a body wall 16, such as the abdominal wall. The purpose of the obturator 10 is to create an incision by piercing, incising, cutting or otherwise penetrating the body wall 16 to allow the trocar body 12 to be left extending through the incision after the obturator 10 is removed. The trocar body 12, including the cannula 13, can then serve as an access port through the body wall 16 and into a body cavity 18.

Figures 2, 3, 4:
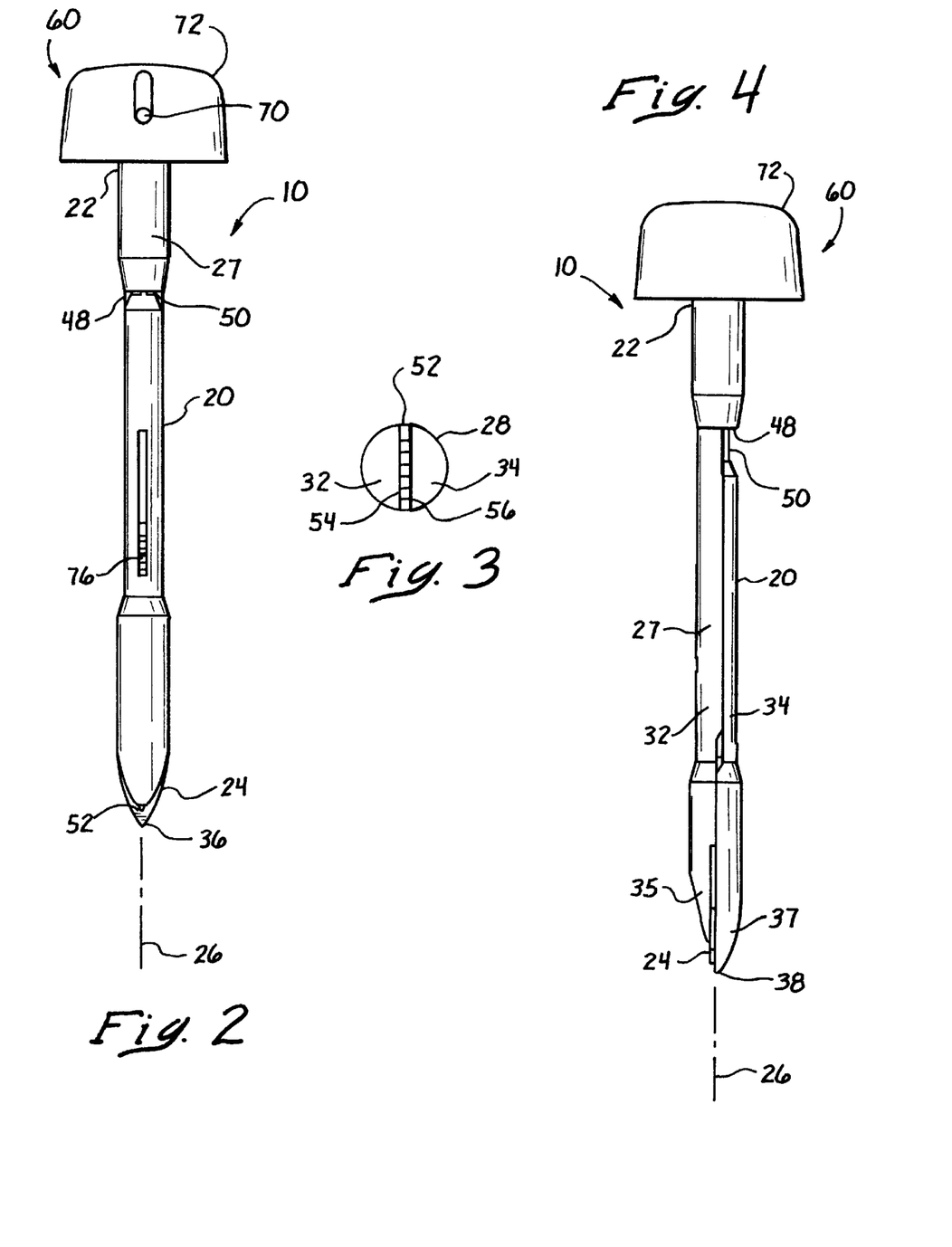
FIG. 2 is a side view of the obturator of FIG. 1 shown in the cutting position.
FIG. 3 is a bottom view of the obturator of FIG. 1.
FIG. 4 is a side view of the obturator of FIG. 1 rotated ninety degrees and shown in the safety position.
Figure 5:
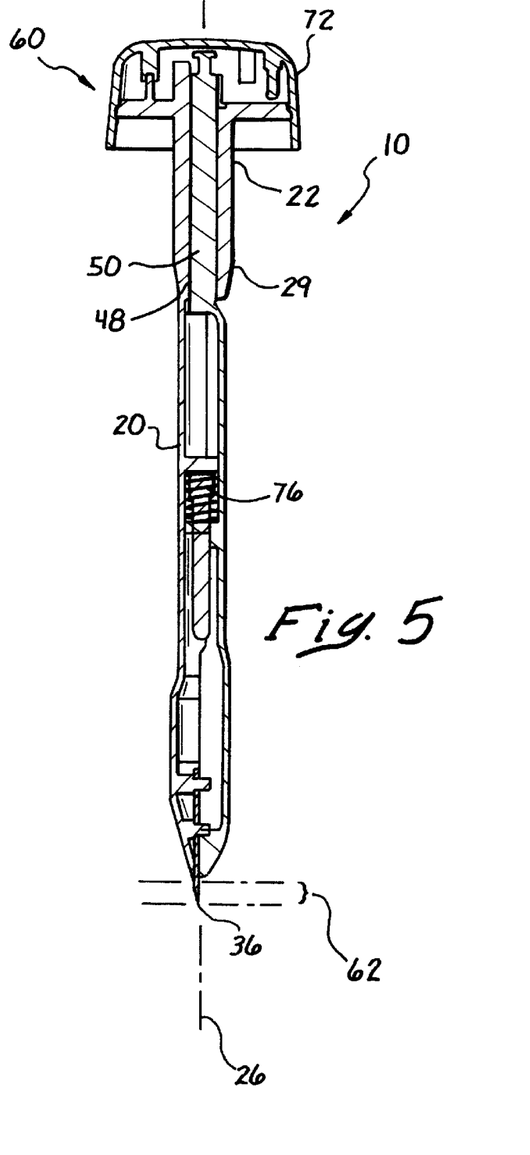
FIG. 5 is a sectional view of the obturator of FIG. 2.
Figure 6:
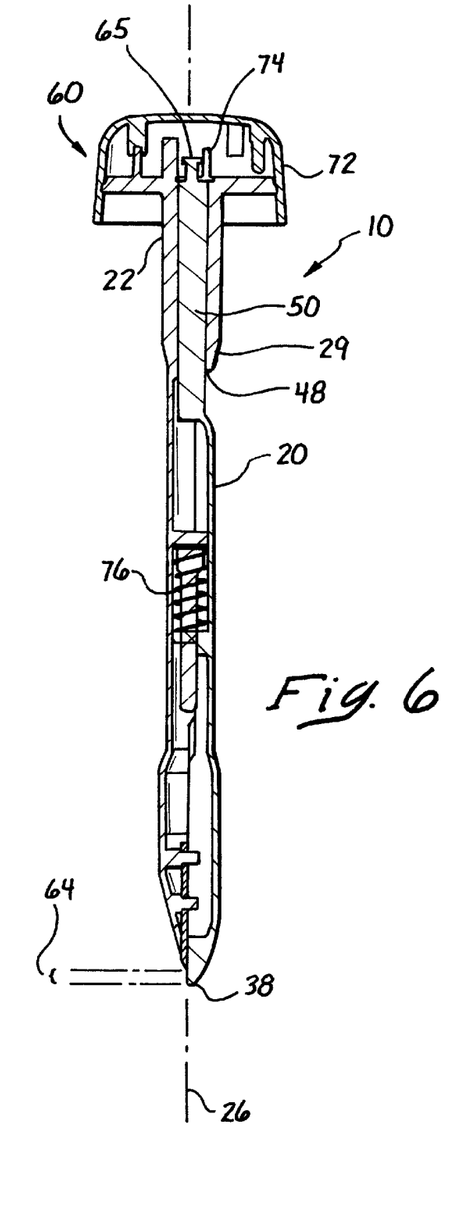
FIG. 6 is a sectional view of the obturator of FIG. 4.

Referring now to FIGS. 2 and 3, the obturator 10 may comprise an elongate shaft 20 extending between a proximal end 22 and a distal end 24 along a longitudinal axis 26. The shaft 20 includes an outer surface 27 which forms a cross section along its length and a tip 30 at the distal end 24. Preferably, the outer surface 27 is generally cylindrical about the axis 26 with a circular or similarly shaped cross section. This circular cross section may be advantageous when passing the shaft 20 through the trocar body 12 and the cannula 13 as shown in FIG. 1. However, the outer surface 27 of the shaft 20 may also have a plurality of differing shaped cross sections as well as differing radial sizes.

Referring to FIGS. 4 through 10, the shaft 20 may include a plurality of shaft portions such as a first shaft portion 32 and a generally opposing second shaft portion 34. The first shaft portion 32 may extend along the longitudinal axis 26 and terminate distally to form a first tip portion 35. Preferably, this first tip portion 35 includes a sharp distal tip 36. The second shaft portion 34 may also extend along the longitudinal axis and terminates distally to form a second tip portion 37. Preferably, this second tip portion 37 includes a blunt distal tip 38. Thus, the shaft portions 32 and 34 extend along the longitudinal axis 26 in juxtaposition to form at least a portion of the shaft 20. Preferably, each of the shaft portions 32 and 34 extends from the proximal end 22 to the distal end 24 of the shaft 20, where at least one of the first and second tip portions 35 and 37 defines the shaft tip 30.

Figure 9:
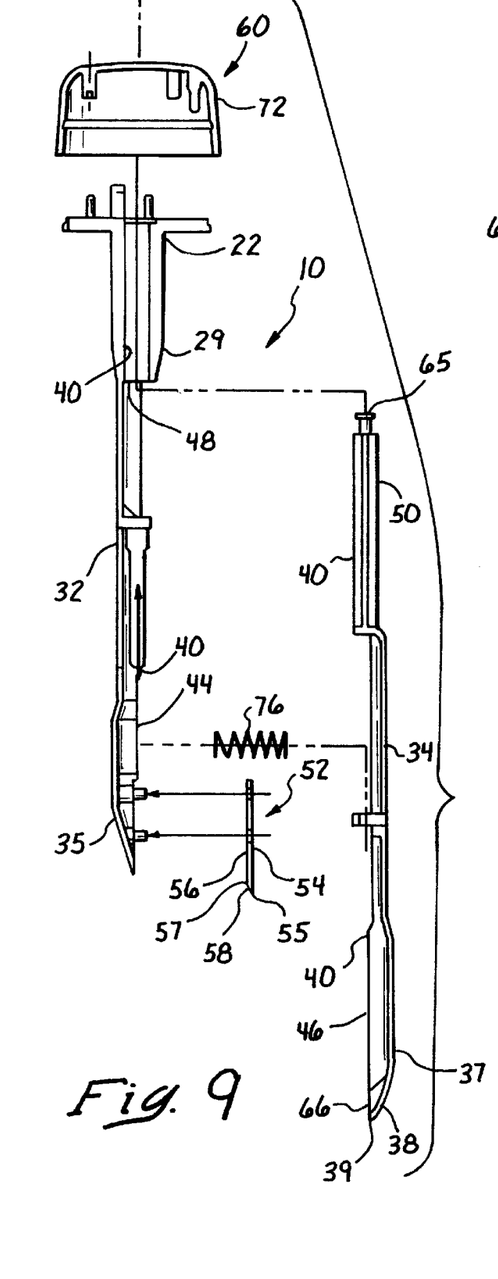
FIG. 9 is an exploded sectional view of the obturator of FIG. 1.
Figure 10:
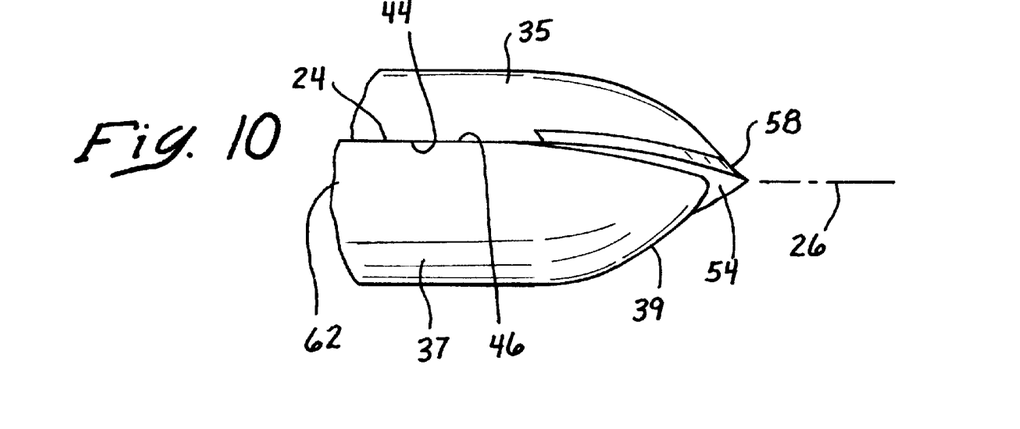
FIG. 10 is a partial perspective view of the distal end of the obturator shaft of FIG. 2.
Figure 11:
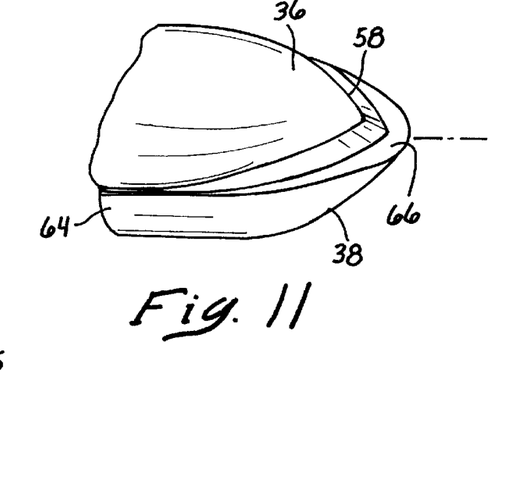
FIG. 11 is a partial perspective view of the distal end of the obturator shaft of FIG. 4.

As illustrated in FIG. 9, each of the portions of the shaft 32 and 34 extend radially from an inner surface 40 to the outer surface 27. The inner surfaces 40 may extend axially in juxtaposition to each other and be generally opposing and at least of portion of the inner surfaces 40 may be aligned along the longitudinal axis 26. In this configuration, the shaft portions 32 and 34 together form outer surface 27 and thus, the cross section 28 of the shaft 20.

At least one of the shaft portions, such as the first shaft portion 34, may have a cross section with the general shape of a section of a circle or other similar shape. The first and second shaft portions 32 and 34 may even be asymmetrical along a portion of their lengths. However, other shapes may also be used as well as additional shaft portions.

The first shaft portion 32 is configured to be longitudinally movable relative to the second shaft portion 34. To facilitate this movement, the inner surfaces 40 on each of the shaft portions 32 and 34 may be configured with an opposing planar section 42 or planar sections aligned with the longitudinal axis 26. These opposing planar sections 42 allow the inner surfaces 40 on each shaft portion to slidably move against each other. Preferably, the first tip portion 35 includes a first planar side 44 and the second tip portion 37 includes an opposing and generally co-planar second planar side 46. Each of the planar sides 44 and 46 may be configured for slidable contact along the longitudinal axis 26. All of opposing planar sections 42 and opposing planar sides 44 and 46 may be configured for relatively frictionless sliding contact and may include a frictionless surface finish.

The first shaft portion 32 and the second shaft portion 34 may be configured so as to be longitudinally slidable against each other without moving radially apart. Preferably, this configuration includes coupling the shaft portions 32 and 34 together. More specifically, the first shaft portion 32 may include a proximally located bore 48 through which a proximal end 50 of the second shaft portion 34 slidably passes. The bore 48 and the proximal shaft portion end 50 may be aligned along the longitudinal axis 26. The bore 48 and the proximal shaft portion end 50 are preferably cylindrical, but this is not essential and other cross sectional shapes may also be used. Alternatively, a bore may be configured through the second shaft portion 34 or even through the overall shaft 20, with the first shaft portion 32 having a proximal shaft portion for passage through the bore.

A slidable joint or other coupling means may also be used to maintain the first and second shaft portions 32 and 34 radially together. As an example, one of the inner surfaces 40 may include a longitudinal section having a tongue configuration. The opposing inner surface 40 may comprise a longitudinal section having a grooved configuration for slidably containing the tongue. Other means for retaining the shaft portions radially together may include a sleeve ring which surrounds a portion of the shaft 20. However, in this configuration, the sleeve ring should have a very limited axial length and be disposed along a proximal portion 22 of the shaft 20. In addition, the sleeve ring must not surround the tip portions 35 and 37. Alternatively, other configurations and devices may also be used.

Referring now, back to FIGS. 4 through 11, a blade 52 having a first major surface 54 and a second major surface 56 may be coupled to the first shaft portion 32 and particularly, to the first tip portion 35 to define the sharp distal tip 36. The blade 52 may be a generally flat member with the major surfaces 54 and 56 being generally parallel to each other and to the longitudinal axis 26. Preferably, the second major surface 54 is directly attached to the first tip portion 35 to fixedly connect the blade 52 with the first shaft portion 32. This connection may be accomplished with adhesives, fasteners or the like. Alternatively, the blade 52 may be an integral part of the first tip portion 35. The first major surface 56 may be a planar surface and may extend at least partially along the longitudinal axis of the shaft 26. Preferably, the first major surface 54 forms at least part of the planar side 44 of the first tip portion 35.

The sharp distal tip 36 may be configured through a bevel 58 which extends from a distal edge 57 of the second major surface 56 to a distal edge 55 of the distally extending first major surface 54. Thus, the beveled surface 58 creates a sharp edge 36 which extends across the width of the first major surface 52. This sharp edge 36 may extend across the full cross section 28 of the shaft 20 and may include a rounded triangular shape having progressively distal positions.

An actuating mechanism 60 may be connected to the proximal end 22 of the shaft 20 to facilitate the relative longitudinal movement of the first shaft portion 32 and the second shaft portion 34. This relative movement of the shaft portions 32 and 34 allows the configuration of the shaft tip 30 to be primarily dependent on whether the first tip portion 35 extends distally of the second tip portion 37 or alternatively, whether the second tip portion 37 extends distally of the first tip portion 35. The actuating mechanism 60 may be coupled to either or both of the shaft portions 32 and 34 for the relative movement therebetween. However, the actuating mechanism 60 may preferably be coupled to the proximal end 50 of the second shaft portion 34 and configured to allow movement of the second tip portion 37. This configuration maintains the first shaft portion 32 as a fixed shaft portion and allows the second shaft portion 34 to be a movable shaft portion. The first shaft portion 32 may preferably be the fixed shaft portion due to the potentially high relative mass of the blade 52.

The actuating mechanism 60 may be configured for axially moving the first and second shaft portions 32 and 34 between a first, or cutting position 62 and a second, or safety position 64. The actuating mechanism 60 may be coupled with a shaft block 65 which is coupled to the second shaft portion 34. Movement of the shaft block 65 by the actuating mechanism 60 moves the second shaft portion between the cutting and safety positions 62 and 64. A lock may be provided within the actuating mechanism 60 for securing the obturator 10 in the safety position 64 once resistance is sensed against the first shaft portion 32. The actuating mechanism 60 may be constructed in the accordance with the disclosure of U.S. Pat. No. 5,599,347, which issued Feb. 4, 1997, and which is fully incorporated herein by reference.

The actuating mechanism 60 may also include an actuator 70 for arming the obturator 10 such that the distal end 24 of the shaft 20 may be moved from the safety position 64 to the cutting position 62. The actuator 70 may be a handle or similar device which extends outwardly from a housing 72 that surrounds the actuating mechanism 60. The actuator 70 may be coupled with a release mechanism 74 which is adapted to mechanically release the lock securing the second shaft portion 34 in the safety position 64.

In the cutting position 62, the second shaft portion 34 is moved proximally relative to the first shaft portion 32. This movement retracts the second tip portion 37 proximally of the first tip portion 35 to expose a sharp configuration and particularly, to expose the sharp distal tip 36. The cutting position 62 facilitates the piercing or otherwise cutting of the body wall 16 by the shaft tip 30 at the distal end 24 of the shaft 20.

In the safety position 64, the second shaft portion 34 is moved distally relative to the first shaft portion 32. This movement extends the second tip portion 37 distally of the first tip portion 35 until the blunt distal end 38 covers and blocks any access to the sharp distal tip 36. The blunt distal tip 38 has a generally rounded and blunt outer configuration with a flat inner surface 66 aligned with the second planer surface 46. Preferably, the flat inner surface 66 is coplanar with and comprises at least part of the second planar side 46. This allows the blunt distal tip 38 to axially slide against the opposing planer first major surface of the blade 52 between the cutting position 62 and the safety position 64. The safety position 64 inhibits the cutting of the body wall 26 or any other tissue by providing a blunt shaft tip 30 and by covering and thus, shielding the sharp edge of the sharp distal tip 36.

Figures 7, 8:
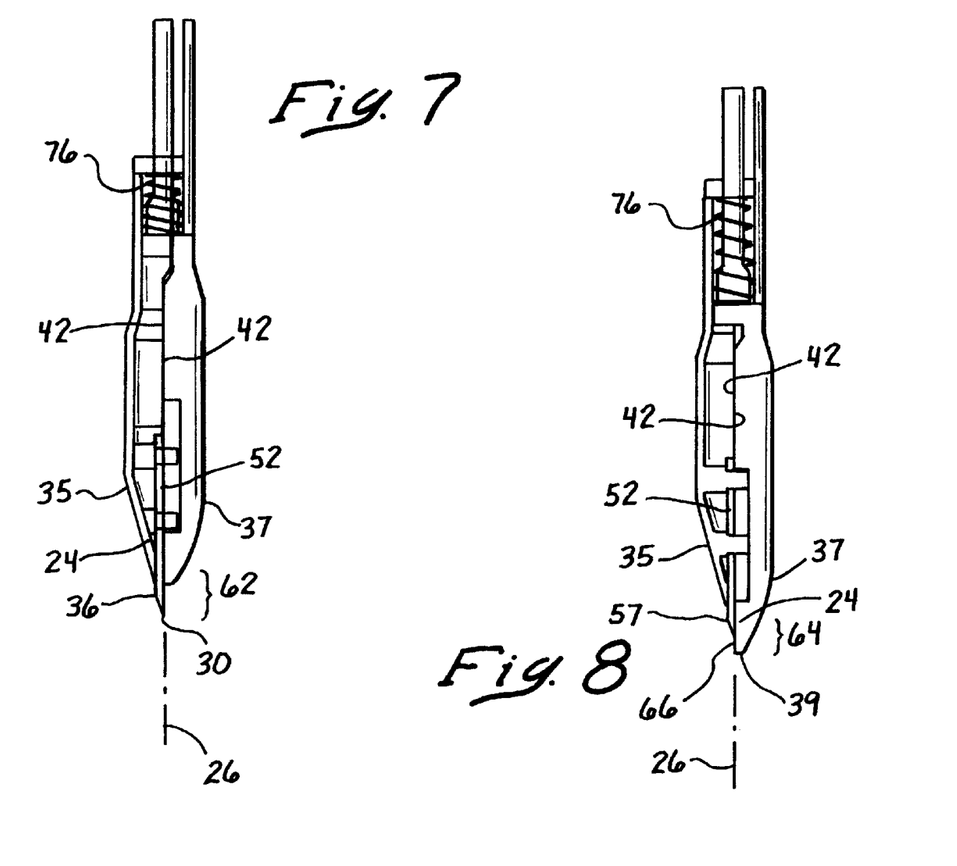
FIG. 7 is an enlarged partial sectional view of the obturator of FIG. 5.
FIG. 8 is an enlarged partial section view of the obturator of FIG. 6.

A biasing element 76 may be coupled to the first and second shaft portions 32 and 34 for biasing the second shaft portion 34 to the second or safety position 64. This allows the obturator 10 to normally be in the safety position 64 and prevents inadvertent cutting, contamination or damage. The biasing element may be a spring which couples the first shaft portion 32 to the second shaft portion 34. The spring 76 may be maintained in compression to maintain a constant pressure directed distally against the second shaft portion 34, as best illustrated in FIG. 7. When the obturator 10 is in the cutting position, the second shaft portion 34 is moved proximally and the spring 76 is further compressed. This compression results in additional force being directed by the biasing element 76 in an effort to move the obturator 10 into the safety position, as best illustrated in FIG. 8. This increased biasing force advantageously results in a quicker transition time from the cutting position 62 to the safety position 64.

Referring back to FIGS. 1 through 11, a method if using an obturator according to the principles of the present invention will be described. The method includes the step of providing an obturator such as the obturator 10 of the present invention. In particular, the provided obturator 10 may include a shaft 20 having a longitudinal axis 26 and an outer surface 27 which extends between a proximal end 22 and a distal end 24. The shaft 20 includes a first shaft portion 32 which defines part of the outer surface 27 and has a first inner surface 44. The first shaft portion 32 extends distally to a sharp distal tip 36. The shaft 20 also includes a second shaft portion 34, which also defines part of the outer surface 27 and includes a second inner surface 46. The second shaft portion 34 extends distally to a distal tip 38 having a rounded blunt configuration and a blunt distal edge 39. Each of the inner surfaces 44 and 46 may be formed to include a portion of the longitudinal axis 26. An actuating mechanism may be coupled to the shaft 20 to facilitate the axially movement of the first shaft portion 32 relative to the second shaft portion 34 and between a first or cutting position 62 wherein the shaft tip 30 is characterized by the sharp distal tip 36 and a second or safety position 64 wherein the shaft tip is characterized by the blunt distal tip 38.

The obturator 10 may be inserted into a trocar body 12 and through a cannula 13 until the distal end 24 of the shaft 20 extends distally through the cannula. When a surgeon or other operator is ready to pierce or otherwise penetrate the body wall 16, the actuating mechanism 60 may be actuated or otherwise armed. When armed, the obturator 10 allows relative axial movement between the shaft portions 32 and 34 and between the cutting and safety positions 62 and 64. More specifically, arming the actuating mechanism 60 releases the lock securing the obturator 10 in the safety position 64 and allows the second shaft portion 34 to be moved proximally to expose the sharp distal tip 36 on the first shaft portion 32.

The shaft tip 30 may be pushed against the body wall 16. The resistive pressure of the body wall 16 may be used to move the second shaft portion 34 proximally and exposes the sharp distal tip 36 which punctures or otherwise penetrates the body wall. Alternatively, the second shaft portion 34 may be manually moved proximally and into the cutting position 62 to expose the sharp distal tip 36. Thus, the second tip portion 37 is disposed in the cutting position 62 when the first tip portion 35 initially contacts the body wall. When the body wall 16 comes in contact with the second tip portion 37, it may be biased or otherwise moved distally to the safety position 64. This biasing may include sliding the blunt distal tip 38 along the inner surface 44 of the first shaft portion 32 until the blunt edge 39 slides distally of and covers the sharp distal tip 36. This prevents access to the sharp edge of the sharp distal tip 36 and prevents further cutting within the body cavity 18.

The step of moving the second shaft portion 34 may include moving the second shaft portion 34 in proximity to the inner surface 44 on the first shaft portion 32 between the cutting position 62 and the safety position 64. Preferably, this movement comprises sliding the second shaft portion 34 axially along the inner surface 44 of the first shaft portion 32.

It will be understood that various modifications can be made to the various embodiments of the present invention herein disclosed without departing from the spirit and scope thereof. For example, various sizes of the obturator and the shaft portions are contemplated as well as various types of construction materials. Also, various modifications may be made in the configuration of the parts and their interaction. Therefor, the above description should not be construed as limiting the invention, but merely as an exemplification of preferred embodiments thereof. Those of skill in the art will envision other modifications within the scope and spirit of the present invention as defined by the claims appended hereto.

I claim:

1. An obturator adapted for use with a trocar and to provide the trocar with characteristics for penetrating tissue forming a body wall, said obturator comprising:

an elongate shaft having a longitudinal axis extending between a proximal end and a distal end;

a tip disposed at the distal end of the shaft and including a first tip portion extending along the axis and having one of a sharp distal tip and a blunt distal tip, and a generally opposing second tip portion extending along the axis and having the other of the sharp distal tip and the blunt distal tip, and wherein said second tip portion is movable longitudinally relative to said first tip portion; and an actuating mechanism connected to the proximal end of the shaft and coupled through the shaft to the second tip portion for moving the second tip portion between a first position wherein the configuration of the shaft tip is dependent on the first tip portion, and a second position wherein the configuration of the shaft tip is primarily dependent on the second tip portion.

2. The obturator recited in claim 1, wherein the first tip portion has the sharp distal tip and the second tip portion has the blunt distal tip; and the first position of the second tip portion is proximal of the second position of the second tip portion.

3. The obturator recited in claim 1, wherein the first tip portion has the blunt distal tip and the second tip portion has the sharp distal tip; and the second tip portion in the second position provides the tip with a sharp configuration.

4. The obturator as recited in claim 1, wherein said first tip portion includes a first planar side and said second tip portion includes a second planar side co-planar with the first planar side.

5. The obturator as recited in claim 4, wherein said first tip portion comprises a blade having a sharp edge formed, at least in part by the first planar side.

6. The obturator recited in claim 4, wherein the second planar side of the second tip portion is slidable on the first planar side of the first tip portion.

7. The obturator recited in claim 5, wherein the first planar side of the first tip portion and the second planar side of the second tip portion are disposed along the longitudinal axis of the shaft.

8. The obturator recited in claim 5, wherein the sharpened edge is formed by the first planar side and a bevel extending toward the first planar side with progressive distal positions along the longitudinal axis of the shaft.

9. The obturator recited in claim 1, wherein the second tip portion is movable axially between the first position and the second position.

10. The obturator recited in claim 1, wherein the second tip portion is disposed in the first position when the first tip portion initially contacts the body wall, and the second tip portion is biased to the second position after the body wall contacts the second tip portion in the first position.

11. An obturator, comprising:

a shaft extending between a proximal end and a distal end along a longitudinal axis;

a first shaft portion extending along the longitudinal axis of the shaft and having a sharp distal tip;

a second shaft portion disposed in juxtaposition to the first shaft portion and having a blunt distal tip;

an actuation mechanism coupled to the second shaft portion and adapted for controlling movement of the second shaft portion relative to the first shaft portion between a first position and a second position;

a shaft block included in the actuation mechanism and disposed at the proximal end of the shaft, the shaft block coupled to the second shaft portion and movable with the second shaft portion between the first position and the second position;

a biasing element coupling the first shaft portion and the second shaft portion and adapted for biasing the second shaft portion to the second position; and an actuator coupled with a release mechanism within the actuating mechanism and adapted for releasably restraining the biasing element such that the second shaft portion may be moved to the first position;

wherein the sharp end of the first shaft portion defines the distal end of the shaft in the first position and the blunt end of the shaft defines the distal end of the shaft in the second position.

* * * * *